United States Patent [19]

Kummer et al.

[11] Patent Number: 5,514,118
[45] Date of Patent: May 7, 1996

[54] MEASURED DOSE EYE DROPPER

[76] Inventors: Frederick J. Kummer, 344 82nd St., Brooklyn, N.Y. 11209; Victor H. Frankel, 39 Cramercy Park N., New York, N.Y. 10010

[21] Appl. No.: 237,424

[22] Filed: May 3, 1994

Related U.S. Application Data

[63] Continuation of Ser. No. 996,190, Dec. 23, 1992, abandoned.

[51] Int. Cl.⁶ .................................................. A61M 35/00
[52] U.S. Cl. ........................... 604/298; 222/67; 222/450; 604/289
[58] Field of Search ..................... 604/289, 298, 604/294, 295; 141/24–27; 222/420, 422, 424, 212, 67, 450

[56] References Cited

U.S. PATENT DOCUMENTS

| | | | |
|---|---|---|---|
| 718,801 | 1/1903 | Strauss | 222/422 |
| 1,422,778 | 7/1922 | Petcher | 141/24 |
| 1,762,059 | 6/1930 | Jones | 222/422 |
| 2,237,213 | 4/1941 | Brown | 222/420 X |
| 3,416,499 | 12/1968 | Wilmot | 222/422 |
| 4,173,226 | 11/1979 | Shell | 604/295 |
| 4,317,473 | 3/1982 | Gaydos | 222/420 X |
| 4,671,330 | 6/1987 | Miles | 141/24 |
| 4,779,768 | 10/1988 | St. Amand | 604/295 X |
| 4,917,274 | 4/1990 | Asa et al. | 604/295 X |
| 4,927,062 | 5/1990 | Walsh | 604/295 X |
| 5,040,706 | 8/1991 | Davis et al. | 604/295 X |
| 5,048,727 | 9/1991 | Vlasich | 604/295 X |
| 5,127,553 | 7/1992 | Weinstein | 222/420 X |

*Primary Examiner*—Mary Beth Jones
*Assistant Examiner*—Dennis Ruhl
*Attorney, Agent, or Firm*—Stephen C. Glazier

[57] ABSTRACT

The present invention uses an adaptation of a float valve installed within the barrel of the eye dropper at the time of manufacture. This prevents the operator of the eye dropper from intaking more than the predetermined amount of liquid into the barrel of the eye dropper. Once the eye dropper is filled, the operator expels the entire amount of liquid taken into the eye dropper, which is the predetermined amount.

10 Claims, 2 Drawing Sheets

5,514,118

MEASURED DOSE EYE DROPPER

This is a continuation of application Ser. No. 07/996,190, filed Dec. 23, 1992, now abandoned.

BACKGROUND OF THE INVENTION

The field of this invention is eye droppers. More specifically, the field of invention is measured dose eye droppers. The present invention is the first eye dropper to automatically administer a predetermined dose of liquid.

Eye droppers are well known. For medical purposes they commonly have a graduated scale on the side of the transparent barrel to allow the measurement and administration of a specific amount of liquid. However, obtaining the required amount of liquid in any particular application requires some minimal level of manual dexterity and visual acuity by the operator . This is a particular problem for people who lack manual dexterity, such as arthritics, and for people who are temporarily or permanently impaired in their vision.

The present invention avoids these deficiencies and provides for an automatic and accurate delivery by the eye dropper of a predetermined volume of liquid. An individual embodiment of this invention is limited to its single preselected volume and is not adapted to provide different select volumes in one embodiment.

SUMMARY OF THE INVENTION

The present invention uses an adaptation of a float valve installed within the barrel of the eye dropper at the time of manufacture. When the eye dropper is empty, the flow valve is open and liquid may be drawn into the eye dropper. When the predetermined amount of liquid is taken into the eye dropper, the float valve closes and no more liquid may be taken in. This prevents the operator of the eye dropper from drawing more than the predetermined amount of liquid into the barrel of the eye dropper. Once the eye dropper is filled, the operator expels the entire amount of liquid taken into the eye dropper, which is the predetermined amount. The liquid in the dropper can be expelled at any time, and is not inhibited by the float valve.

This invention allows use of an eye dropper to accurately and consistently administer a predetermined volume of liquid medicine, even by an operator who has limited manual dexterity or is blind.

DESCRIPTION OF A PREFERRED EMBODIMENT

Figure 1:
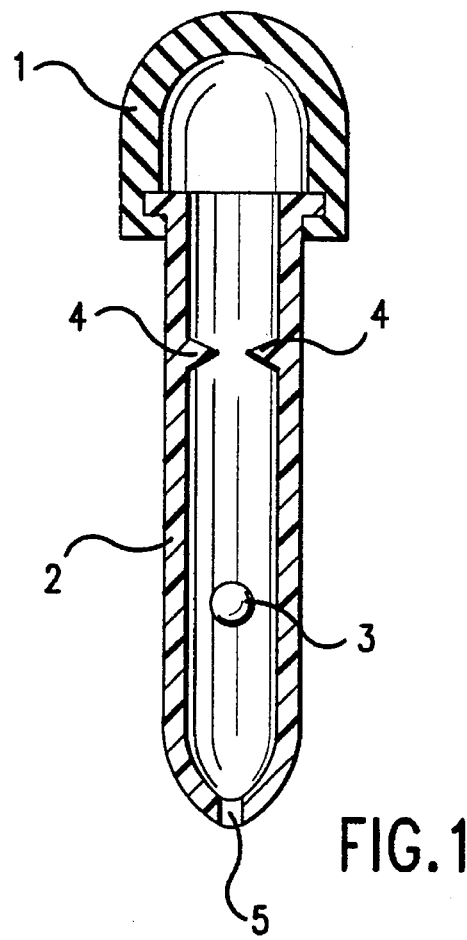
FIG. 1 shows a cross-sectional view of the present invention.

FIG. 1 shows a cross sectional view of the present invention. The eye dropper has a squeezable bulb 1 attached over the larger end of the hollow barrel 2. A small lightweight float 3 is contained inside the barrel 2. The inside of the barrel contains an annular internal ridge 4. The ridge 4 has an inner diameter that is smaller than the outer diameter of the float 3. The smaller end of the barrel 2 has an opening 5. The diameter of the opening 5 is smaller than the outer diameter of the float 3.

The float 3 with the ridge 4 act together as a float valve. As liquid is drawn into the cylinder 2 through the opening 5, the float 3 rises up until it is constrained by the annular ridge 4. At that point of constraint, the float 3 prevents further intake of liquid into the barrel 2, and the eye dropper has taken in its predetermined volume of liquid which may then be delivered. In the design phase of a specific embodiment, the annular ridge 4 can be located to adjust the predetermined volume of liquid. In the manufacturing phase, enough incongruity is manufactured between the float 3 and the opening 5 to permit air to be expelled from the barrel 2 when the bulb 1 is squeezed while the barrel 2 is in the inverted vertical position.

Figure 2:
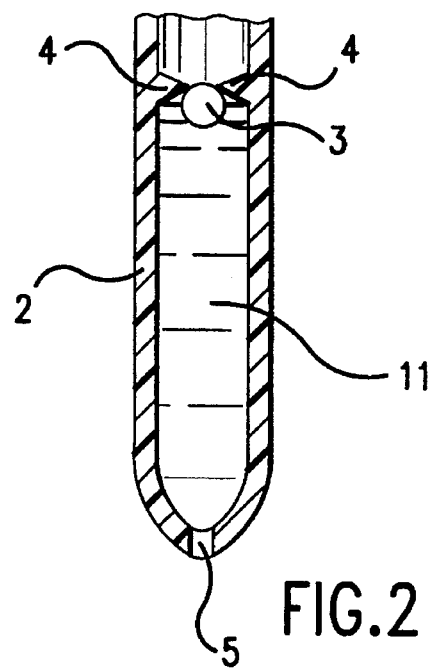
FIG. 2 shows a cross-sectional of the open end of the present invention.
Figure 3A:
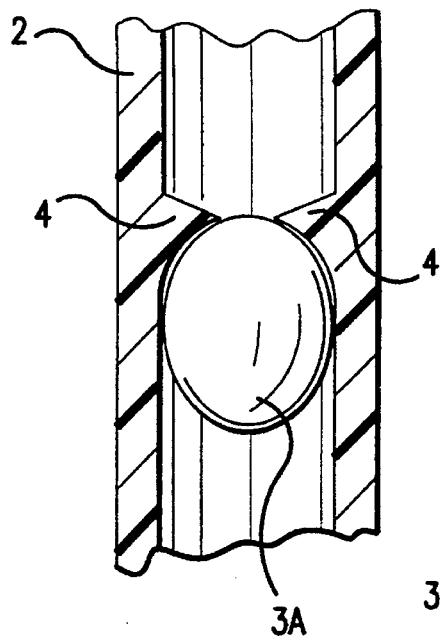
FIG. 3A shows a cross sectional partial view of the present invention with an ovoid shaped float.
Figure 3B:
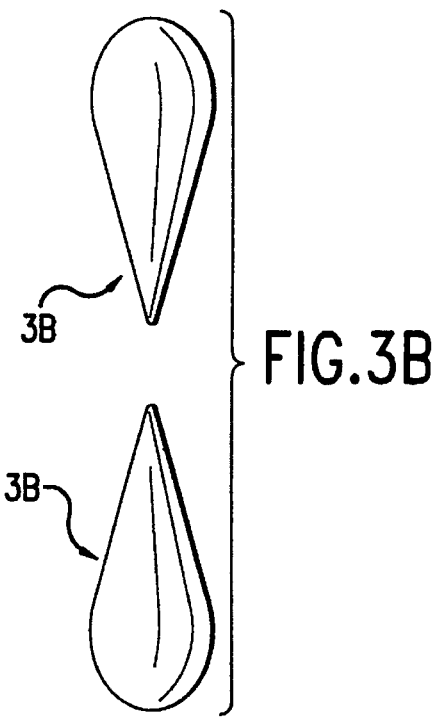
FIG. 3B shows a teardrop shaped float of the present invention.
Figure 3C:
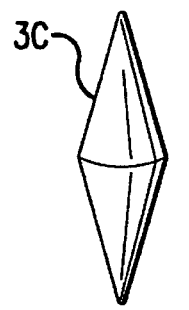
FIG. 3C shows a double conical shaped float of the present invention.
Figure 3D:
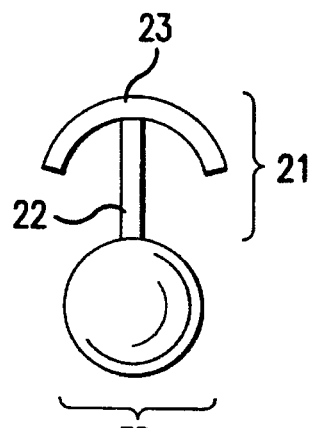
FIG. 3D shows another shape of a float suitable for use with the present invention.
Figure 3E:
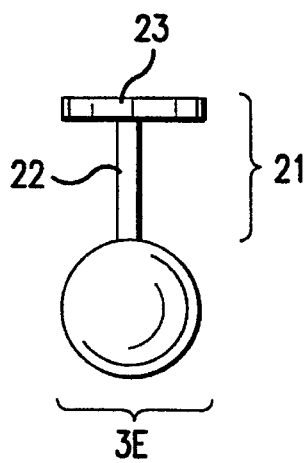
FIG. 3E shows yet another shape of a float suitable for use with the present invention.

FIG. 2 shows a close up of cross-sectional view of the tip of the present invention while the invention is filled with the predetermined volume of medicine. The barrel 2 is shown with the float 3 and the opening 5 and the annular ridge 4. Also shown is the liquid medicine 11 filling the volume of the barrel 2 below the annular ridge 4 and above the opening 5. The float 3 is made to be less dense than the likely fluid to be used, so that the float 3 floats on top of the fluid in the cylinder 4. The seat between the float 3 and the annular ridge 4 must be tight enough to prevent fluid passing around the annular ridge 4 when the float 3 is seated therein.

FIG. 3 shows a cross section of the invention with a variety of float shapes. Again the barrel 2 and the annular ridge 4 are shown with the float 3. Float 3A is an ovoid shaped float. Float 3B is a teardrop shape (and its point, as shown, can be oriented toward either end of the barrel 2), and float 3C is a double conical shape. The float 3 can be hollow, and should be somewhat soft or rubbery to fit and seal better at the top at the annular ridge 4. The float 3 must be less dense than the liquid intended to be used by the eye dropper, so that the float 3 will float. But the float 3 should be hard enough so that it cannot be jammed either in the annular ridge 4 or the opening 5. The float 3, barrel 2, and bulb 1 can be made of various well known plastics. The barrel 2 can be made of glass.

Figure 4:
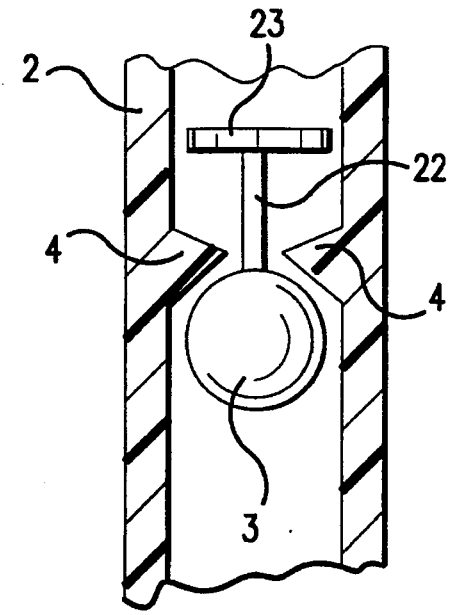
FIG. 4 shows a cross-sectional partial view of the present invention utilizing the float as shown in FIG. 3E.

FIG. 4 shows a cross-sectional view of part of the present invention with yet another type of float 3. The barrel 2 is shown with the annular ridge 4. The float 3 is fixed in place by a molded tab 21 which compresses when the float 3 is inserted inside the barrel 2. The flexible molded tab 21 has a narrow stem 22 of an outer diameter which is smaller than the inner diameter of the annular ridge 4, and a wide flexible flap 23 on top of the stem 22, the flap 23 having a outer diameter greater than the inner diameter of the annular ridge 4.

The present invention can be manufactured in the same way and with the same materials as a conventional eye dropper, except for the unique features described herein. The float 3 can be inserted into the barrel after manufacture by pressing it past the annular ridge 4 after insertion through the large opening in the barrel 2 at the end made to receive the bulb 1, prior to installation of the bulb 1 on the barrel 2. In FIG. 4, the molded tab 21 keeps the float 3 in the vicinity of the annular ridge 4 and away from the vicinity of the opening 5. This facilitates any required exhalation of air after the liquid is drawn into the barrel 2. This also will allow an alternative method of assembly where the outside diameter of the float 3 is smaller than the inside diameter of the opening 5. The float 3 then can be inserted through the opening 5 and the flexible tab 21 could be pressed through the annular ridge 4. Float 3D shows the compression of the flexible tab 21 at the point of pressing past the annular ridge 4. Float 3E in FIG. 4 shows the configuration of tab 21 after such pressing.

The invention can also be made in another series of steps. The barrel 2 can be first manufactured as a cylinder without pinching the opening 5. Then the annular ridge 4 can be made inside the barrel 2. Then the float can be dropped into the barrel 2, between the ridge 4 and the opening 5. Then the opening 5 can be heated and drawn to the smaller final opening diameter. This can be done whether barrel 2 is glass or plastic.

The embodiments illustrated and discussed in the specification are intended only to teach those skilled in the art the best way known by the inventors to make and use this invention. Nothing in the specification should be considered as limiting the scope of the present invention. Many changes could be made by those skilled in the art to produce equivalent systems without departing from the invention. The present invention should be limited only by the following claims and their legal equivalents.

The term "eye dropper" is defined herein to mean much more than the narrow meaning of a smaller dropper for eyes. Herein, "eye dropper" is a general term meaning any device used to transfer liquid from a bottle or other location to a body part (for example, an eye, ear, nose, or mouth) or to another container or location. The term is not limited in size, and can be quite large (for example, the "turkey baster" size). It also includes devices with tubes, barrels, cylinders, and pipettes (for example, a titration pipette). It also includes all manner of drawing liquid into the device, including squeeze bulbs, vacuum pumps, and mouth suction. It includes all manner of expelling liquids from the device, including gravity, squeeze of bulbs, forced air, and mouth blowing.

We claim:

1. A measured dose eye dropper comprising:
    (a) a hollow cylindrical barrel having a first end and, a second end, and an inner surface,
    (b) a means for providing suction to draw a fluid into said hollow cylindrical barrel, the first end of the barrel configured to receive the means for providing suction to draw the fluid, the barrel having a small opening at the second end configured to permit passage of said fluid,
    (c) a float with an outer diameter, said float being disposed within the barrel and having a density which is less than a density of the fluid, and
    (d) an internal annular ridge defined on the inner surface of the hollow barrel, said ridge having an inner diameter smaller than the outer diameter of the float and being located between the float and the first end of the barrel at a distance from the second end of the barrel so that when a pre-determined amount of liquid is drawn into the barrel, the float floats against the annular ridge preventing further fluid from being drawn into the barrel, the pre-determined amount being equal to a volume of space in the barrel between the second end of the barrel and float when the float floats against the ridge.

2. The invention in claim 1, wherein the float has a spherical shape.

3. The invention in claim 1, wherein the float has an ovoid shape.

4. The invention in claim 1, wherein the float has a teardrop shape.

5. The invention in claim 1, wherein the float has a double conical shape.

6. The invention in claim 1, wherein the float has a flexible molded tab consisting of a narrow stem, having an outer diameter which is smaller than the inner diameter of the annular ridge, and a wide, flexible, flap on top of said narrow stem, the flap having an outer diameter greater than the inner diameter of the annular ridge.

7. The invention in claim 1, wherein the means for providing suction is one of a flexible squeeze bulb and a suction pump.

8. The invention in claim 1, wherein said inner surface has a circular cross section.

9. The invention in claim 1, wherein said means for providing suction provides the suction to said volume of space in the barrel.

10. The invention in claim 7, wherein said flexible squeeze bulb is attached over said first end of the barrel and has an interior in direct communication with said volume of space in said barrel.

* * * * *